United States Patent
Westlund

(10) Patent No.: US 7,013,181 B2
(45) Date of Patent: Mar. 14, 2006

(54) CORONARY VEIN LEAD HAVING COMBINATION FIXATION FEATURES WITH LUMEN RESTRICTION AND METHOD THEREFOR

(75) Inventor: Randy Westlund, Minneapolis, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 496 days.

(21) Appl. No.: 10/328,763

(22) Filed: Dec. 23, 2002

(65) Prior Publication Data

US 2004/0122499 A1    Jun. 24, 2004

(51) Int. Cl.
*A61N 1/00*    (2006.01)
(52) U.S. Cl. .................... 607/120; 607/128; 604/256
(58) Field of Classification Search ........ 607/104–105, 607/120, 126–128; 604/256
See application file for complete search history.

(56) References Cited

U.S. PATENT DOCUMENTS

| | | | |
|---|---|---|---|
| 4,957,118 A | 9/1990 | Erlebacher | 128/785 |
| 5,562,723 A | 10/1996 | Rugland et al. | 607/126 |
| 5,669,790 A | 9/1997 | Carson et al. | 439/668 |
| 5,681,280 A | 10/1997 | Rusk et al. | 604/95 |
| 6,192,280 B1 | 2/2001 | Sommer et al. | 607/122 |
| 6,240,322 B1 | 5/2001 | Peterfeso et al. | 607/126 |

FOREIGN PATENT DOCUMENTS

| | | |
|---|---|---|
| EP | 0779080 | 12/1995 |
| GB | 2067411 | 1/1980 |

*Primary Examiner*—Mark Bockelman
(74) *Attorney, Agent, or Firm*—Schwegman, Lundberg, Woessner & Kluth, P.A.

(57) ABSTRACT

A lead assembly includes insulative tubing with at least one tine coupled thereto, and a lumen extends through the tubing. The tine has a first position that extends away from the exterior of the tubing, and a second compressed position. In the second compressed position, the tine at least partially compresses the lumen.

22 Claims, 3 Drawing Sheets

CORONARY VEIN LEAD HAVING COMBINATION FIXATION FEATURES WITH LUMEN RESTRICTION AND METHOD THEREFOR

TECHNICAL FIELD

The present invention relates generally to a lead for use within vessels such as coronary veins. More particularly, it pertains to a lead having combination fixation features and lumen restriction.

BACKGROUND

A cardiac pacing system includes a battery powered pulse generator and one or more leads for delivering pulses to the heart. Current pulse generators include electronic circuitry for determining the nature of an irregular rhythm, commonly referred to as arrhythmia, and for timing the delivery of a pulse for a particular purpose. The pulse generator is typically implanted into a subcutaneous pocket made in the wall of the chest. Insulated wires called leads attached to the pulse generator are routed subcutaneously from the pocket to the shoulder or neck where the leads enter a major vein, usually the subclavian vein. The leads are then routed into the site of pacing, for example, within a cardiac vein. The leads are electrically connected to the pulse generators on one end and are electrically connected to the heart on the other end. Electrodes on the leads provide the electrical connection of the lead to the heart. The leads deliver the electrical discharges from the pulse generator to the heart.

After the electrode assembly is positioned at a desired location within the heart, it is desirable to provide some method for securing the electrode assembly at that location. One approach is to use a passive device which has structure to allow for tissue growth surrounding the structure to affix the electrode assembly to the heart. Another approach is to use an active device where mechanical fixation devices are used to firmly anchor the electrodes in the heart. One type of mechanical fixation device used is a corkscrew, or a helix. During placement of the lead, the tip of the lead travels intravenously through veins and the heart. While traveling through the veins, the helix at the tip of the lead may snag or attach to the side wall of the vein, which is undesirable.

During use, the lead provides and receives critical information to and from the heart. The lead, therefore, must remain in sufficient operative condition without interference from entry of bodily fluids. To prevent entry of bodily fluids into the lead, a seal is provided. Conventional leads use O-rings or puncture seals to seal the distal end of the lead from entry of bodily fluids. The O-ring seals can be difficult to manufacture due to dimensional constraints which also affects the extension/retraction mechanism of the lead, as well as the effectiveness of the seal. Puncture seals also may increase the difficultly of using an over-the-wire lead, since the seal affects the maneuverability of the lead over the guide wire. Furthermore, the seals can increase the friction between the guide wire and the lead. The friction makes it more difficult to guide the lead over the guide wire.

Accordingly, there is a need for a lead which is sufficiently sealed from the environment. What is further needed is a seal which does not interfere with the maneuverability of the lead over the guide wire.

SUMMARY

A lead assembly is provided that includes insulative tubing extending from a proximal end to a distal end. The insulative tubing has a lumen extending through the distal end, and the lumen is defined by an inner surface of the insulative tubing. At least one conductor is disposed within the insulative tubing, where the at least one conductor extends to the proximal end of the insulative tubing. An electrode assembly is electrically coupled with the at least one conductor.

At least one tine is coupled to an exterior of the tubing at a connecting location. The tine has a first position that extends away from the exterior, and a second compressed position. In the second compressed position, the tine at least partially compressing the lumen. The lumen has a first cross-sectional shape in the first position, a second cross-sectional shape in the second position.

Several options for the lead assembly are as follows. For example, in one option, passage of fluid through the lumen to the proximal end is substantially reduced when the tine is placed in the second position. In another option, a width across the lumen is reduced by at least 50% when the tine is placed in the second compressed position. In yet another option, a width across the lumen is reduced by at least 75% when the tine is placed in the second compressed position. Optionally, the inner surface of the lumen has at least two portions contacting each other when the at least one tine is in the second compressed position, or the inner surface of the insulative tubing forms a seal to the lumen when the at least one tine is in the second compressed position. The insulative tubing, in one option, has a first wall thickness at the connecting location and a second wall thickness at the proximal end, and the first wall thickness is less than the second wall thickness. In yet another option, the at least one tine is formed of a first material, and the insulative material is formed of a second material, and the first material is more rigid than the second material.

In another embodiment, a lead assembly includes insulative tubing extending from a proximal end to a distal end, where the insulative tubing has a lumen extending through distal end. The lumen is defined by an inner surface of the insulative tubing. At least one conductor is disposed within the insulative tubing, where the at least one conductor extends to the proximal end of the insulative tubing. An electrode assembly is electrically coupled with the at least one conductor.

At least one tine is coupled to an exterior of the tubing at a connecting location, where the at least one tine has a first position extending away from the exterior and a second compressed position. In the second compressed position, the at least one tine at least partially compresses the lumen. In the second position, the lumen has non-circular cross-sectional shape.

Several options for the lead assembly are as follows. For instance, in one option, the at least one tine is formed of a first material, and the insulative material is formed of a second material, and the first material is more rigid than the second material. The lead assembly further includes a means for decreasing passage of fluid through the lumen. In yet another option, portions of the inner surface of the lumen contact each other to substantially reduce passage through the lumen. The insulative tubing, in one option, has a first wall thickness at the connecting location and a second wall thickness at the distal end, and the first wall thickness is less than the second wall thickness.

A method is provided including forming a lead assembly including providing insulative tubing extending from a proximal end to a distal end, where the insulative tubing has a lumen extending through distal end, and the lumen is defined by an inner surface of the insulative tubing. The method further includes providing at least one tine coupled to an exterior of the tubing at a connecting location, the at least one tine having a first position extending away from the exterior of the insulative tubing, in the first position the lumen has a first cross-sectional shape. The method also includes inserting the lead assembly through a passage, compressing the at least one tine to a second compressed position, and compressing the lumen with the at least one tine to decrease a width of the lumen to substantially reduce fluids from passing through the lumen to the proximal end, in the second position the lumen has a second cross-sectional shape, where the first cross-sectional shape is different than the second cross-sectional shape.

Several options for the method are as follows. For instance, in one option, the method further includes contacting a portion of the inner surface with another portion of the inner surface. Optionally, compressing the lumen includes decreasing the lumen and forming a seal with the inner surface of the lumen to substantially prevent fluids from passing therethrough. In yet another option, the method further includes forming a first wall thickness adjacent to the at least one tine and forming a second wall thickness adjacent to the proximal end of the tubing, where the first wall thickness is thinner than the second wall thickness. The method further includes, in one option, partially collapsing the at least one tine, where the lumen is not substantially modified by partially collapsing the at least one tine. Providing at least one tine in one option, includes providing a first tine opposite a second tine, and the first and second tines are collapsed against the tubing to at least partially compress the lumen.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
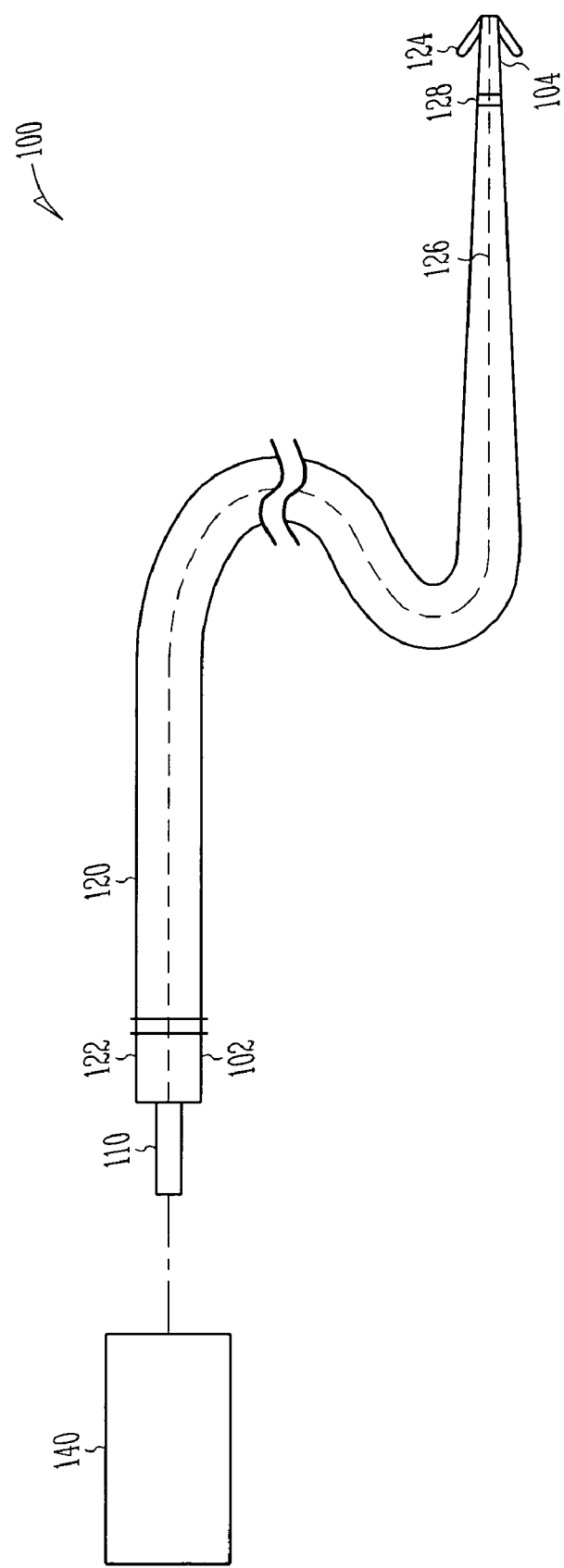
FIG. 1 is a block diagram illustrating a lead assembly constructed in accordance with one embodiment.
Figure 2:
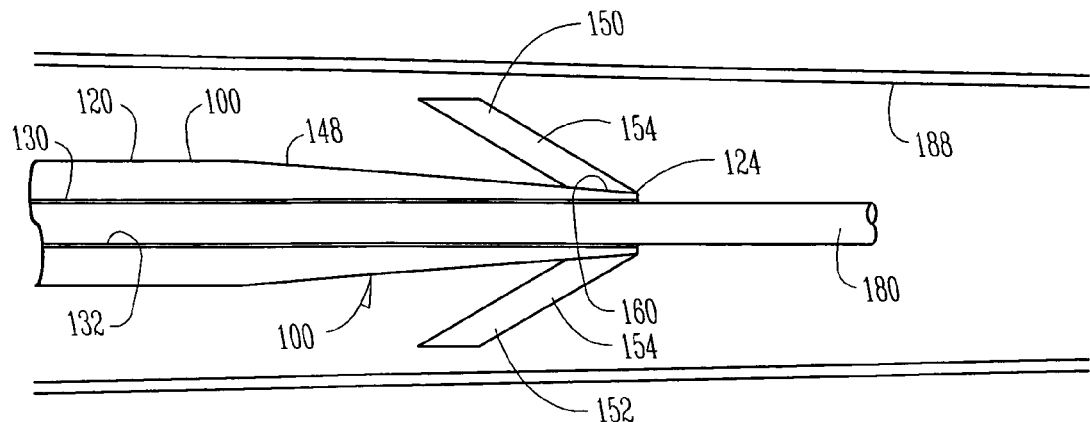
FIG. 2 is a cross-sectional view illustrating a portion of the lead assembly constructed in accordance with one embodiment.

A lead assembly is provided that includes fixation features for an open lumen lead, which also assist in preventing fluids from entering the lead. FIG. 1 illustrates one example of a coronary vein lead 100. The lead 100 has a lead proximal end 102 and a lead distal end 104 and includes a connector terminal 110, and a lead body 120. The lead 100 attaches to a pulse sensor and generator 140. In one embodiment, the lead 100 is constructed and arranged for insertion into the coronary sinus. The lead body 120 has a number of electrodes, in one option, in the lead distal end 104 which is implanted in a coronary vein 188 (FIG. 2). The connector terminal 110 electrically connects the various electrodes and conductors within the lead body 120 to the pulse sensor and generator 140. The pulse sensor and generator 140 contains electronics to sense various pulses of the heart and also produce pulsing signals for delivery to the heart. The pulse sensor and generator 140 also contains electronics and software necessary to detect certain types of arrhythmias and to correct for them.

The lead body 120 extends from a body proximal end 122 to a body distal end 124. In one option, the body distal end 124 is tapered, as shown in FIG. 2. The lead body 120 includes insulative tubing material formed from a polymer biocompatible for implantation, and in one option, the tubing is made from a silicone rubber polymer.

In addition, the lead body 120 optionally has portions which have shape memory characteristics, comprising either a shape memory polymer or a shape memory metal. Referring again to FIG. 1, the lead body contains several electrical conductors 126. The electrical conductors 126 are made of a highly conductive, highly corrosion-resistant material, and are electrically coupled with at least one electrode 128. The electrical conductors 126 carry current and signals between the pulse sensor and generator 140 and the electrodes 128 located at the distal end 104 of the lead 100.

Referring to FIG. 2, the lead body 120 includes a lumen 130 therein, where the lumen 130 has an inner surface 132 therein. The lumen 130 extends through the body distal end 124, and is unencumbered by sealing structure disposed on the inner surface 132 within the lumen 130. The lumen 130 allows for the lead 100 to be implanted over a guide wire 180. After the lead 100 is implanted within, for example, a coronary vein 188, the guide wire 180 is removed. Since there is a lumen 130, if no seal is present, fluids would be permitted to enter the lumen 130, possibly affecting the performance of the lead 100. In contrast, traditional membrane seals disposed within the lumen 130 can affect the maneuverability of the lead 100 over the guide wire 180, since the guide wire 180 would be disposed through the seal.

Figure 3:
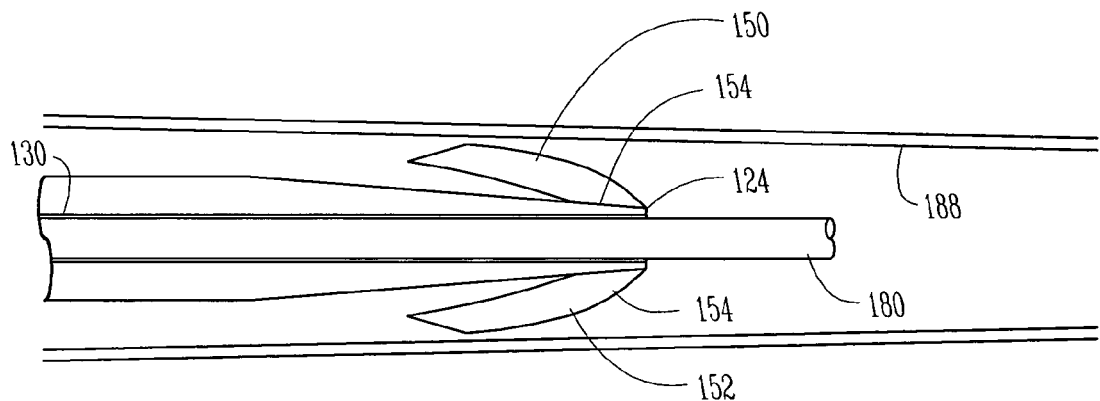
FIG. 3 is a cross-sectional view illustrating a portion of the lead assembly constructed in accordance with one embodiment.
Figure 4:
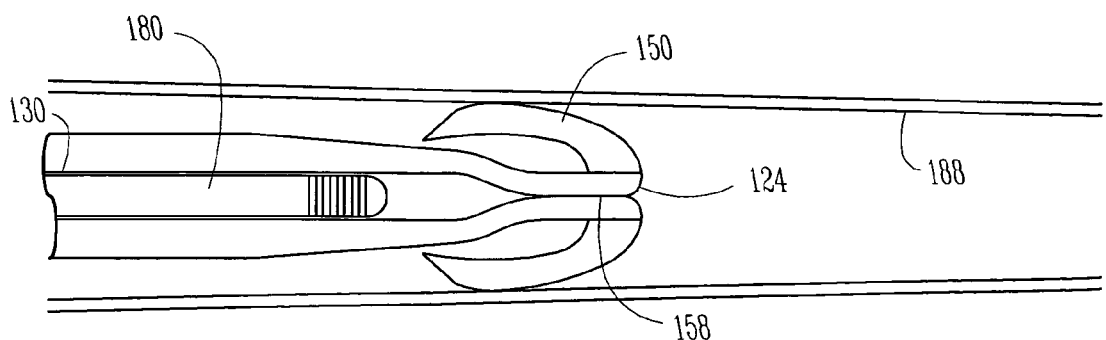
FIG. 4 is a cross-sectional view illustrating a portion of the lead assembly constructed in accordance with one embodiment.

At least one tine 150 is coupled with an exterior surface 148 of the insulative tubing, and optionally the at least one tine 150 is coupled at the distal end 124. The at least one tine 150, in one option, includes multiple tines 152. In one option, at least two tines 154 are disposed opposite one another on the tubing as shown in FIGS. 2–4. The at least one tine 150 is coupled with the lead body 120 at a connecting location 160. The at least one tine 150, in a first position shown in FIG. 2, extends away from the lead body 120.

Figure 5:
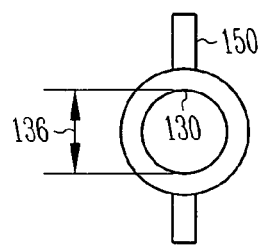
FIG. 5 is an end view illustrating the lead assembly constructed in accordance with one embodiment.

As the lead body 120 is disposed in progressively smaller cardiac veins, the at least one tine 150 begins to be compressed against the lead body 120, as shown in FIG. 3, and is ultimately disposed in a second compressed position, as shown in FIG. 4. In the second compressed position, the lumen 130 has a second cross-sectional shape (FIG. 6) that is different than a first cross-sectional shape, where the first cross-sectional shape is shown in FIG. 5. Further, in the second compressed position, the at least one tine 150 at least partially compresses the lumen 130, and optionally at least two portions 158 of the inner surface 132 contact one another, as shown in FIG. 7. The second cross-sectional shape is different than the first cross-sectional shape.

Figure 6:
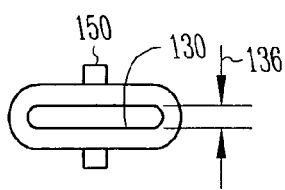
FIG. 6 is an end view illustrating the lead assembly constructed in accordance with one embodiment.
Figure 7:
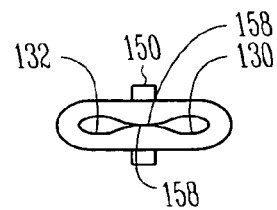
FIG. 7 is an end view illustrating the lead assembly constructed in accordance with one embodiment.
Figure 8:
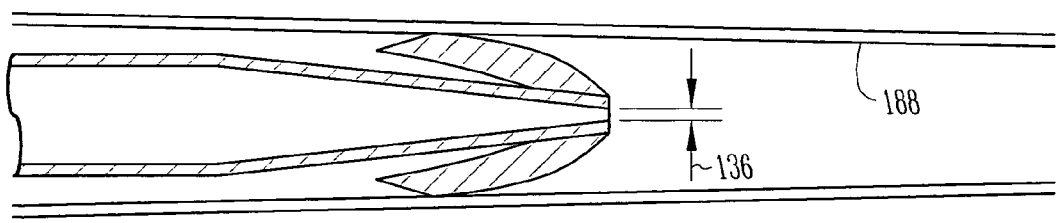
FIG. 8 is a cross-sectional view illustrating a portion of the lead assembly constructed in accordance with one embodiment.

In one option, the second cross-sectional shape is non-circular, as shown in FIG. 6 or 7. In another option, passage of fluid, such as blood, through the lumen to the body proximal end 122 (FIG. 1) is substantially reduced when the at least one tine 150 is placed in the second compressed position. In yet another option, a width 136 across the lumen 130 is reduced by at least 50%, as shown in FIG. 6. In another option, the width 136 across the lumen 130 is reduced by at least 75%, as shown in FIG. 8. In yet another option, the inner surface of the insulative tubing forms a seal to the lumen when the at least one tine is in the second compressed position. The seal is formed, for example by substantially preventing fluid from passing therethrough. Passage through the lumen can be partially closed, or entirely closed to prevent blood from entering through the lumen.

Figure 9:
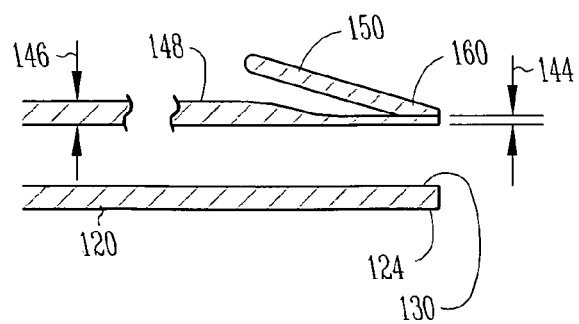
FIG. 9 is a cross-sectional view illustrating a portion of the lead assembly constructed in accordance with one embodiment.

Various embodiments illustrate ways for the at least one tine 150 to at least partially compress the lumen 130, and/or decrease passage of fluid through the lumen. For example, the lumen 130 in combination with the exterior surface 148 of the lead body 120 define a wall thickness therebetween, as shown in FIG. 9. In one option, a first wall thickness 144 at or near the connecting location 160 is thinner than a second wall thickness 146 that is optionally disposed at the body proximal end 122 (FIG. 1) and/or a body distal end 124. The first wall thickness 144 is positioned relative to the at least one tine 150 to allow for the at least one tine 150 to compress against the lead body 120 and allow for the lumen 130 to be thereby compressed.

In another option, the at least one 150 is formed of a first material such as silicone or polyurethane, and the lead body 120 is formed of a second material such as silicone or polyurethane, where the first material is more rigid than the second material. Alternatively, the durometer of the materials are modified to achieve a tine that is more rigid than the body 120. Alternatively, tine geometry at the connecting location, and/or tine length can be used to further facilitate closing of the lumen with the tines.

A method is provided including forming a lead assembly including providing insulative tubing extending from a proximal end to a distal end, where the insulative tubing has a lumen extending through distal end, and the lumen is defined by an inner surface of the insulative tubing. The method further includes providing at least one tine coupled to an exterior of the tubing at a connecting location, the at least one tine having a first position extending away from the exterior of the insulative tubing, in the first position the lumen has a first cross-sectional shape.

The method also includes inserting the lead assembly through a passage, for example over a guide wire disposed within the passage. The passage becomes increasing smaller in width and/or diameter as the lead assembly progress further into the passage, for example, in branch vessels of a cardiac vein. As the lead assembly is disposed through the passage, the at least one tine is compressed by the passage to a second compressed position. In compressing the at least one tine, the lumen is compressed by the at least one tine to decrease a width of the lumen to substantially reduce fluids from passing through the lumen to the proximal end. In the second position, the lumen has a second cross-sectional shape, where the first cross-sectional shape is different than the second cross-sectional shape. The guide wire is removed before or after the lumen is placed in the cross-sectional shape.

Several options for the method are as follows. For instance, in one option, the method further includes contacting a portion of the inner surface of the lumen with another portion of the inner surface to substantially prevent fluids from passing therethrough. Optionally, compressing the lumen includes decreasing the lumen and forming a seal with the inner surface of the lumen to substantially prevent fluids from passing therethrough. In yet another option, the method further includes forming a first wall thickness adjacent to the at least one tine and forming a second wall thickness adjacent to the proximal end of the tubing, where the first wall thickness is thinner than the second wall thickness.

The method further includes, in one option, partially collapsing the at least one tine, where the lumen is not substantially modified by partially collapsing the at least one tine. Providing at least one tine in one option, includes providing a first tine opposite a second tine, and the first and second tines are collapsed against the tubing to at least partially compress the lumen. The guide wire is optionally retracted within the lead assembly prior to or after the decrease in the lumen.

Advantageously, the at least one tine provides a fixation feature within a passage, such as a cardiac vein, and furthermore provides a way to seal the lumen within the lead. For over-the-wire leads, these are beneficial features since the sealing features also do not interfere with the maneuverability of the lead assembly over the guide wire.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present application. The scope of the invention should, therefore, be determined with reference to the appended claims, along with the full scope of equivalents to which such claims are entitled.

What is claimed is:

1. A lead assembly comprising:

insulative tubing extending from a proximal end to a distal end;

the insulative tubing having a lumen extending through the distal end, the lumen defined by an inner surface of the insulative tubing;

at least one conductor disposed within the insulative tubing, the at least one conductor extending to the proximal end of the insulative tubing;

at least one electrode assembly electrically coupled with the at least one conductor;

at least one tine coupled to an exterior of the tubing at a connecting location; and the at least one tine having a first position extending away from the exterior and a second compressed position, the at least one tine at least partially compressing the lumen in the second compressed position, in the first position the lumen has a first cross-sectional shape, and in the second position the lumen has a second cross-sectional shape, where the first cross-sectional shape is different than the second cross-sectional shape.

2. The lead assembly as recited in claim 1, wherein passage of fluid through the lumen to the proximal end is substantially reduced when the tine is placed in the second position.

3. The lead assembly as recited in claim 1, wherein a width across the lumen is reduced by at least 50% when the tine is placed in the second compressed position.

4. The lead assembly as recited in claim 1, wherein a width across the lumen is reduced by at least 75% when the tine is placed in the second compressed position.

5. The lead assembly as recited in claim 1, wherein the inner surface of the lumen has at least two portions contacting each other when the at least one tine is in the second compressed position.

6. The lead assembly as recited in claim 1, wherein the insulative tubing has a first wall thickness at the connecting location and a second wall thickness at the proximal end, and the first wall thickness is less than the second wall thickness.

7. The lead assembly as recited in claim 1, wherein the inner surface of the insulative tubing forms a seal to the lumen when the at least one tine is in the second compressed position.

8. The lead assembly as recited in claim 1, wherein the at least one tine is formed of a first material, and the insulative material is formed of a second material, and the first material is more rigid than the second material.

9. A lead assembly comprising:

insulative tubing extending from a proximal end to a distal end;

the insulative tubing having a lumen extending through the distal end, the lumen defined by an inner surface of the insulative tubing;

at least one conductor disposed within the insulative tubing, the at least one conductor extending to the proximal end of the insulative tubing;

at least one electrode assembly electrically coupled with the at least one conductor;

at least one tine coupled to an exterior of the tubing at a connecting location; and the at least one tine having a first position extending away from the exterior and a second compressed position, the at least one tine at least partially compressing the lumen in the second compressed position, in the first position the lumen has a first cross-sectional shape, and in the second position the lumen has non-circular cross-sectional shape.

10. The lead assembly as recited in claim 9, wherein the at least one tine is formed of a first material, and the insulative material is formed of a second material, and the first material is more rigid than the second material.

11. The lead assembly as recited in claim 9, further comprising a means for decreasing passage of fluid through the lumen.

12. The lead assembly as recited in claim 9, wherein portions of the inner surface of the lumen contact each other to substantially reduce passage through the lumen.

13. The lead assembly as recited in claim 9, wherein the insulative tubing has a first wall thickness at the connecting location and a second wall thickness at the distal end, and the first wall thickness is less than the second wall thickness.

14. The lead assembly as recited in claim 9, wherein the insulative tubing is tapered at the distal end.

15. A method comprising:

forming a lead assembly including:

providing insulative tubing extending from a proximal end to a distal end, the insulative tubing having a lumen extending through the distal end, the lumen defined by an inner surface of the insulative tubing;

providing at least one tine coupled to an exterior of the tubing at a connecting location, the at least one tine having a first position extending away from the exterior of the insulative tubing, in the first position the lumen has a first cross-sectional shape, and;

inserting the lead assembly through a passage;

compressing the at least one tine to a second compressed position; and compressing the lumen with the at least one tine to decrease a width of the lumen to substantially reduce fluids from passing through the lumen to the proximal end, in the second position the lumen has a second cross-sectional shape, where the first cross-sectional shape is different than the second cross-sectional shape.

16. The method as recited in claim 15, further comprising contacting a portion of the inner surface with another portion of the inner surface.

17. The method as recited in claim 15, wherein compressing the lumen includes decreasing the lumen and forming a seal with the inner surface of the lumen to substantially prevent fluids from passing therethrough.

18. The method as recited in claim 15, further comprising forming a first wall thickness adjacent to the at least one tine and forming a second wall thickness adjacent to the proximal end of the tubing, where the first wall thickness is thinner than the second wall thickness.

19. The method as recited in claim 15, further comprising partially collapsing the at least one tine, where the lumen is not substantially modified by partially collapsing the at least one tine.

20. The method as recited in claim 15, wherein providing at least one tine includes providing a first tine opposite a second tine, and the first and second tines are collapsed against the tubing to at least partially compress the lumen.

21. The method as recited in claim 15, further comprising positioning the lead assembly over a guide wire inserted within the passage.

22. The method as recited in claim 21, further comprising retracting the guide wire within the lead body prior to compressing the lumen with the at least one tine.

* * * * *